(12) United States Patent
Willsie et al.

(10) Patent No.: US 8,540,635 B2
(45) Date of Patent: Sep. 24, 2013

(54) MEDICAL DIAGNOSTIC IMAGING WITH HARDWARE GENERATED REGION OF INTEREST BORDER

(75) Inventors: Todd D. Willsie, Seattle, WA (US); William M. Derby, Jr., Bethlehem, PA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 1243 days.

(21) Appl. No.: 11/827,679

(22) Filed: Jul. 12, 2007

(65) Prior Publication Data

US 2009/0018440 A1 Jan. 15, 2009

(51) Int. Cl.
*A61B 8/00* (2006.01)
*G06K 9/00* (2006.01)
*G06K 9/48* (2006.01)

(52) U.S. Cl.
USPC ............ 600/443; 600/437; 382/128; 382/199

(58) Field of Classification Search
USPC ....................................................... 382/283
See application file for complete search history.

(56) References Cited

U.S. PATENT DOCUMENTS

| | | | |
|---|---|---|---|
| 5,573,001 A | 11/1996 | Petrofsky et al. | |
| 6,106,466 A * | 8/2000 | Sheehan et al. | 600/443 |
| 6,337,925 B1 * | 1/2002 | Cohen et al. | 382/199 |
| 6,537,221 B2 * | 3/2003 | Criton et al. | 600/454 |
| 6,996,272 B2 * | 2/2006 | Chen et al. | 382/173 |
| 7,022,073 B2 * | 4/2006 | Fan et al. | 600/437 |
| 7,343,031 B2 * | 3/2008 | Pedrizzetti et al. | 382/128 |
| 7,507,204 B2 * | 3/2009 | Shim et al. | 600/443 |
| 7,826,884 B2 * | 11/2010 | Baumgart | 600/407 |
| 8,005,309 B2 * | 8/2011 | Taketa et al. | 382/240 |
| 2002/0072671 A1 * | 6/2002 | Chenal et al. | 600/450 |
| 2004/0002652 A1 | 1/2004 | Phelps et al. | |
| 2004/0227976 A1 * | 11/2004 | Pavlov et al. | 358/1.18 |
| 2006/0074312 A1 * | 4/2006 | Georgescu et al. | 600/437 |
| 2007/0036404 A1 * | 2/2007 | Li | 382/128 |
| 2008/0170765 A1 * | 7/2008 | D'sa et al. | 382/128 |

* cited by examiner

*Primary Examiner* — Long V. Le
*Assistant Examiner* — Angela M Hoffa

(57) ABSTRACT

A system and method for generating a border of a region of interest of an image, such as a medical image, are disclosed. Imaging data is acquired for generation of an image. A region of interest of the image is determined. A display value is allocated to a plurality of pixels, respectively, based on color or tissue information from the imaging data. If at least one pixel corresponds to a border of the region of interest, a border value is allocated to the at least one pixel substantially at the same time as when the display value is allocated. The image having the border of the region of interest is displayed.

23 Claims, 2 Drawing Sheets

MEDICAL DIAGNOSTIC IMAGING WITH HARDWARE GENERATED REGION OF INTEREST BORDER

BACKGROUND

The present invention relates to medical imaging. In particular, a system and method of generating a border for a region of interest is provided.

A variety of medical images are used to diagnose abnormalities or ailments, monitor bodily functions and anatomy, or guide medical professionals during medical procedures. For example, medical images are generated via magnetic resonance imaging ("MRI"), computed tomography ("CT"), X-ray scans, positron emission tomography ("PET"), ultrasound, as well as other modalities. Within these images, a medical professional may want to concentrate on a specific region or area, commonly referred to as a region of interest ("ROI").

For example, in ultrasound, a flow region for color imaging may be denoted by using ROI. The color image data shows blood flow or other motion. A border, having a border color, is used to define the dimensions of the ROI. Using an input device, a user may move the ROI to scan different parts of the image. The border of the ROI is generated as a graphics overlay. For example, when imaging data is acquired, the imaging system allocates display values for generation of the image, such as an ultrasound image showing tissue and/or blood flow information. After the generation of the image, the border color is superimposed on the image.

Using software to overlay a border of the ROI requires superimposition and memory retrieval. However, as imaging systems are reduced in size, less and less area is available for large video graphics cards as well as additional memory for storing video data. Also, by using a software graphics overlay for the border of the ROI, a lag phenomenon may occur when a user pans the ROI about a display due to the superimposition of data on stored video data.

BRIEF SUMMARY

By way of introduction, the preferred embodiments described below include an imaging system with a processor for allocating values for generation of an image. As imaging data is acquired, display values are allocated to a plurality of pixels to generate an image based on the imaging data. Border values associated with a border of a region of interest within the image are allocated at substantially the same time as the display values. The image includes these border values as display values. An image is displayed, and the image includes the border of the region of interest without a graphic overlay.

According to a first aspect, a method of providing a border for a region of interest is provided. Imaging data is acquired for generation of an image. A region of interest of the image is determined. A display value is allocated to a plurality of pixels, respectively, based on color or tissue information from the imaging data. If at least one pixel corresponds to a border of the region of interest, a border value is allocated to the at least one pixel substantially at the same time as when the display value is allocated. The image having the border of the region of interest is displayed.

According to a second aspect, a computer-readable medium has stored therein instructions executable by a processor. The instructions include acquiring ultrasound data for generation of an image. A region of interest of the image is determined. Color or grey scale values are mapped to a plurality of pixels. The mapping is a function of flow, tissue or flow and tissue information from the ultrasound data. If at least one pixel corresponds to a border of the region of interest, a border value is allocated to the at least one pixel substantially at the same time as when the color or grey scale value is allocated.

According to a third aspect, an ultrasound system for providing a border for a region of interest is provided. A transducer is operable to acquire ultrasound data. A processor is operable to assign display values as a function of the ultrasound data and as a function of a border of a region of interest. A display is operable to display an image having the border of the region of interest without a graphic overlay.

The present invention is defined by the following claims, and nothing in this section should be taken as a limitation on those claims. Further aspects and advantages of the invention are discussed below in conjunction with the preferred embodiments.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

A hardware generated ROI border system and method are used in imaging systems, such as a handheld ultrasound system, to avoid the use of software graphic overlays. A border of any color is automatically added around a color or other ROI without any use of graphics drawing software. Imaging data is acquired and display values including tissue and color information are allocated at substantially the same time as border color values. No software calculations of the ROI border pixels are required and no graphics drawing commands are necessary. An additional benefit is that alignment of the color ROI and the border is not subject to a delay that can create a visual artifact.

Figure 1:
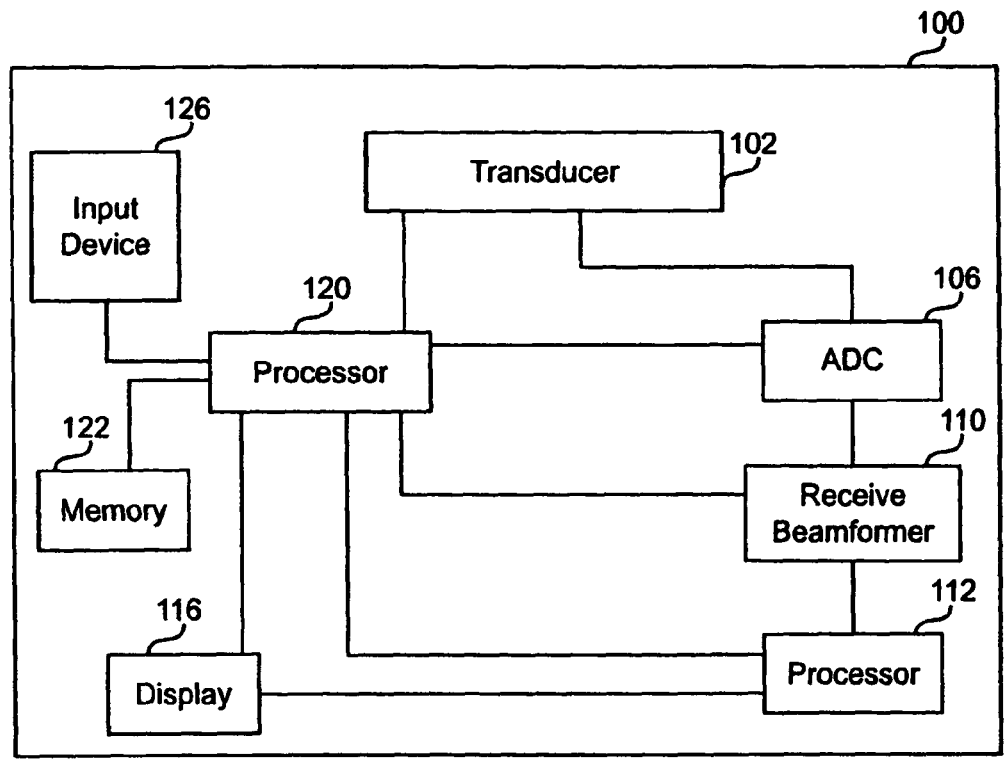
FIG. 1 is a diagram of one embodiment of an imaging system for generating an image with a border of a region of interest.

FIG. 1 shows one embodiment of an imaging system 100. The imaging system 100 is a computed tomography ("CT") scanner, a magnetic resonance imaging ("MRI") system, an ultrasound system, a positron emission tomography ("PET") scanner, or any known or future medical or non-medical imaging system. In other embodiments, the imaging system 100 is a computer, a workstation, server, and/or an image database system.

In one embodiment, the imaging system 100 is an ultrasound system. Any ultrasound imaging system 100 may be used. In one embodiment, the imaging system 100 is a cart based imaging system. In another embodiment, the imaging system 100 is a portable system, such as a briefcase-sized system or laptop computer based system. Other embodiments include handheld ultrasound systems. For example, one or more housings are provided where the entire system is small and light enough to be carried in one or both hands and/or worn by a user. In another example, a transducer is in one housing to be held by a person, and the imaging components and display are in another housing to be held by a person. Coaxial cables connect the two housings. The entire handheld system weighs less than about 6 pounds, but may weigh more. For example, the handheld system weighs about 2 pounds or less. A single housing for an entire handheld system may be provided.

The imaging system 100 includes, but is not limited to, a transducer 102, an analog-to-digital converter ("ADC") 106, a receive beamformer 110, a processor 112, a display 116, an input device 126, a processor 120, and a memory 122. Additional, different, or fewer components may be provided. For example, probe electronics and a transmit beamformer are provided. Also, the processor 112 and the processor 120 may be combined into one processor. The ADC 106 may be a part of the receive beamformer 110, and the input device 126 and the display 116 may be separate from but operable to communicate with the imaging system 100. Any or all of the electronics may be integrated as one module in a single housing.

The processor 120 is in communication with the memory 122, the display 116, the input device 126, the transducer 102, the ADC 106, the receive beamformer 110, and the processor 112. The processor 120 may be in communication with more or fewer components. The processor 120 is a main processor, such as a microprocessor, or a plurality of processors operable to communicate with electronics of the imaging system 100. The processor 120 is operable to control the various electronics and logic of the imaging system 100. The memory 122 is any known or future storage device. The memory 122 is a non-volatile and/or volatile memory, such as a Random Access Memory "RAM" (electronic), a Read-Only Memory "ROM" (electronic), or an Erasable Programmable Read-Only Memory (EPROM or Flash memory). The input device 126 includes, but is not limited to, a button, a keyboard, a rocker, a joy stick, a trackball, a voice recognition circuit, a mouse, or any other input device for sending commands. For example, the input device 126 is operable to move or select a ROI of an image.

The transducer 102 is a single transducer element or transducer array or a plurality of transducer arrays, such as a one dimensional linear phased transducer array or a multi-dimensional transducer array. The transducer 102, for example, is in an ultrasound probe connected with an ultrasound system. The transducer 102 is operable to receive acoustic signals and convert the acoustic signals into electrical energy. For example, the transducer 102 is operable to acquire ultrasound data by receiving echo signals. The ultrasound data includes Doppler, B-mode (grey-scale), and other tissue or flow information.

The transducer 102 may have a plurality of elements, such as 64 or 128 elements. However, any number of transducer elements may be used. The transducer elements are formed from transducer material. The transducer material is piezoelectric ("PZT"), ceramic, silicon, semiconductor and/or membrane, but other materials or structures may be used to convert between acoustical and electrical energies. For example, the transducer material is a multi-layered transducer material having at least two layers of transducer material. Alternatively, the transducer material is a semiconductor substrate with one or more flexible membranes (e.g., tens or hundreds for each element) formed within or on the semiconductor substrate. The transducer elements may also include any number of different layers, such as matching layers, flex circuit layers, signal traces, electrodes, a lens and/or a backing block.

The ADC 106 is in communication with the transducer 102. The ADC 106 is a single or a plurality of any known or future analog-to-digital converters operable to sample analog signals, such as echo signals from tissue. For example, ADCs 106 connect with respective elements (channels) of the transducer 102. The elements connect directly to the ADC 106. Alternatively, multiplexers provide for aperture control to connect elements to different channels at different times. To reduce a number of cables, the number of connections from the elements to the ADC 106 may be reduced. Time multiplexing, frequency multiplexing, sub-array mixing, partial beamforming or other processes for combining signals may be used. For example, signals from groups of four or other numbers of elements are combined onto common data paths by sub-array mixing, such as disclosed in U.S. Pat. No. 5,573, 001 or U.S. Published Application No. 20040002652, the disclosures of which are incorporated herein by reference.

The receive beamformer 110 is in communication with ADC 106. Alternatively, the ADC 106 is incorporated into the receive beamformer 110. The receive beamformer is an application specific integrated circuit ("ASIC"), processor, field programmable gate array ("FPGA"), analog components, digital components, integrated components, discrete devices, or combinations thereof. The receive beamformer includes, but is not limited to, delay memories, a delay calculator, and channel adders as well as other electronic circuitry for forming beams.

In one embodiment, the receive beamformer 110 includes a plurality of delays and one or more summers for relatively delaying electrical signals received from the transducer elements and summing the delayed signals. Amplifiers may be provided for apodization. In one embodiment, the delays are implemented as memories for storing channel data. One or more memories may be used. For example, two memories operate in a ping-pong fashion to store data from elements and read data out for beamforming. Each memory stores element data for an entire scan. As one memory is storing, the other memory is outputting. By reading data out of the memory from selected memory locations, data associated with different amounts of delay is provided. The same data may be used for sequentially forming receive beams along different scan lines. Other memories may be used, such as a plurality of first-in, first-out buffers for delaying based on length and/or timing of input into the buffers.

The processor 112 is in communication with the receive beamformer 110. The processor 112 is a digital signal processor, graphics processing unit, main processor, microprocessor, field programmable gate array, analog circuit, digital circuit, or combinations thereof. The processor 112 is a single device or a plurality of processors. For example, the processor 112 is one central processing unit ("CPU"). Alternatively, the processor 112 is a plurality of CPUs in which each CPU is responsible for sampling and/or processing a portion of the data acquired by the imaging system 100.

For example, the processor 112 is a video or graphics processor, detector, filter, scan converter, or combinations thereof. In one embodiment, the processor 112 includes a B-mode and/or Doppler detectors. Intensity and/or motion information is detected from the receive beamformed information. Scan conversion converts from a scan format to a display format, such as from a polar coordinate format to a Cartesian coordinate format. Any now known or later developed processor 112 and/or image processing may be used, such as an FPGA or ASIC.

The processor 112 is operable to assign display values as a function of the ultrasound data and as a function of a border of a ROI. For example, the processor 112 is operable to map color or grey scale values to a plurality of pixels in which the mapping is a function of flow, tissue or flow and tissue information from the ultrasound data. A function, look-up table, or other device or process may be used for mapping display (e.g., RGB or YUV) values from input ultrasound data (e.g., intensity and flow data).

The processor 112 is also operable to generate an ultrasound image having a border of a region of interest without a graphic overlay. The border information is incorporated into the image data, mapping, and/or data input for determining display values.

The display 116 is in communication with the processor 112. The display 116 is any mechanical and/or electronic display positioned for accessible viewing by a doctor or medical professional. For example, the display 116 is a liquid crystal display ("LCD"), printer, or cathode ray tube ("CRT") monitor. The display 116 includes a plurality of pixels operable to show two dimensional ("2D"), three dimensional ("3D"), and/or four dimensional ("4D") images (i.e., the fourth dimension is time, and, therefore, 4D images are a sequence of images that show an object over a time period), such as ultrasound images.

Figure 2:
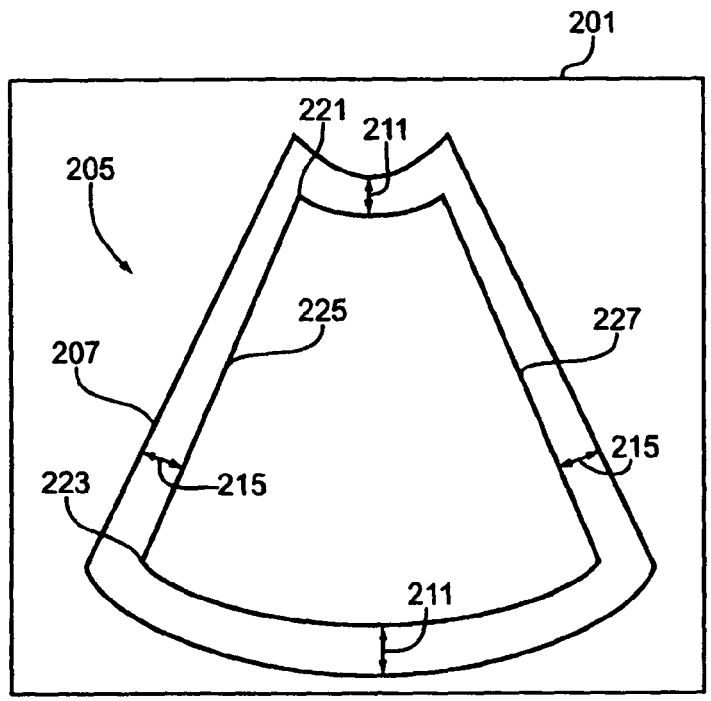
FIG. 2 is an example of an image with a region of interest having a border.

FIG. 2 is an example of an ultrasound image 201 with a ROI 205 having a border 207. For example, the image 201 is an ultrasound image displaying color and grey scale values representing flow and/or tissue. The color values may alternatively or additionally represent tissue motion. The image within the border 207 includes color information, such as information representing motion or flow. The ROI 205 can be moved or shifted via an input device, such as the input device 126, to allow color information to be viewed in different parts of the image 201. The image 201 has any geometrical shape, such as a rectangular or sector shape. The shape of the image 201 may be based on the hardware used for generating the image. Similarly, the border 207 may have any geometrical shape such as, a circular, rectangular, sector shape, hand drawn, tissue structure border, or other shape. The shape of the border 207 may be the same as the shape of the image 201. However, different shapes of the border can be created, but clipping of data or loss of image information may occur.

The border 207 is defined by a border area. For example, the border area has a range width 211, a beam width 215, a range minimum 221, a range maximum 223, a beam minimum 225, and a beam maximum 227 that defines the border 207. Alternatively, borders having shapes other than a sector shape have respective width, maximum, minimum or other dimensions. The dimensions can be altered to customize the size and width of the border 207. The customization may occur before or during imaging, such as between different frames.

Figure 3:
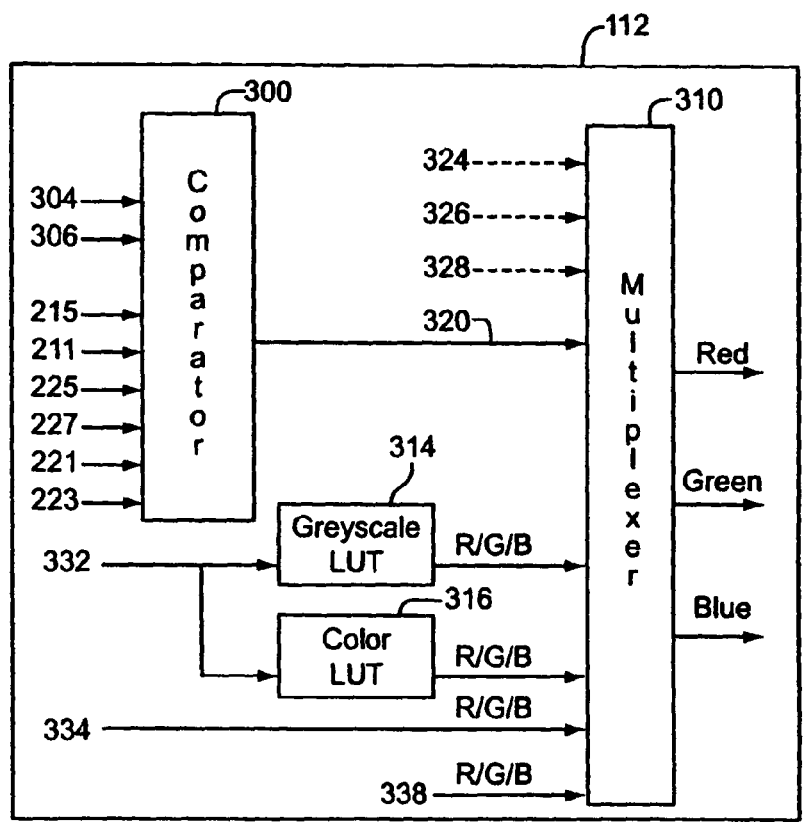
FIG. 3 is an example of a circuit for generating a border of a region of interest.

FIG. 3 is an example of a circuit within the processor 112 for generating a border, such as the border 207, of a ROI, such as the ROI 205. For example, the processor 112 includes, but is not limited to, a comparator 300, a multiplexer 310, a grey-scale look-up-table ("LUT") 314, and a color LUT 316. For each frame or multiple frames, each pixel of a plurality of pixels is assigned a value. For example, the value is a display value corresponding color or tissue information, a border value corresponding to a border of a ROI, and/or a text value corresponding to text to be displayed.

The assignment or allocation of a value to a pixel includes a determination of a video color ("RGB") value based on a prioritization of image information. For example, during each frame or multiple frames, each pixel is assigned video information. Depending on the screen dimensions of the display 116 or customization of image quality or dimensions, the processor 112, for example, assigns a Cartesian coordinate or other location information to each pixel. Then, based on the type of image to be generated as well as the selection of a ROI, the appropriate text, border, tissue, and/or motion or flow RGB value is assigned to the pixel. To determine which video information has priority, a predetermined chain of priority logic is used. The priority logic is stored on the memory 122 and/or multiplexer 310. For example, text information has priority over all other image data, and border information has the second highest priority. If a pixel corresponds to text, border, and tissue information, the text RGB value will be allocated. Alternatively, if a pixel corresponds to only border and tissue information, the border RGB value will be allocated. The determination of what image information corresponds to a respective pixel is implemented by comparator circuitry. Alternatively, other hardware or logic implementations may be used.

For example, the comparator 300 is operable to determine whether at least one pixel of the plurality of pixels corresponds to a border, such as the border 207. The comparator 300 receives pixel location values 304 and 306. The values 304 and 306 are defined as Cartesian coordinates or other location information for a pixel. For example, the value 304 is a range value defined with a Cartesian coordinate for the pixel and the value 306 is a beam value defined with a Cartesian coordinate for the pixel. The comparator 300 also receives the border dimensions, such as the border 207 dimensions of FIG. 2, for the current region of interest of the frame. For example, the comparator receives the range width 211, the beam width 215, the range minimum 221, the range maximum 223, the beam minimum 225, and the beam maximum 227. The comparator is operable to compare the pixel location values 304 and 306 of the pixel with the border dimensions to determine if the pixel is in or on a border area of the border of the ROI.

Any mathematical calculations, functions, or equations may be used to compare the respective values. For example, the following equations represent the comparison logic used to determine if the pixel is in or on the border:

(((beam min 225−beam width 215)<beam value 306≤beam min 225) or (beam max 227≤beam value 306<(beam max 227+beam width 215))) and ((range min 221−range width 211)<range value 304<(range max 223+range width 211))    equation (1):

(((range min 221−range width 211)<range value 304≤range min 221) or (range max 223≤range value 304<(range max 223+range width 211))) and (beam min 225−beam width 215)<beam value 306<(beam max 227+beam width 215))    equation (2):

Alternatively, other equations comparing dimensions of any geometrical shapes with pixel locations may be used. Comparisons are made for each of the pixels to determine is the pixel is within the border.

A value 320 is used as a designation of whether a pixel corresponds to the border or not. For example the value 320 is a flag bit that has a value "0" if the pixel being analyzed is not in or on a border area of the border and has a value "1" if the pixel is in or on the border area of the border. The value 320 is transmitted to the multiplexer 310.

Comparisons of whether a pixel corresponds to tissue information, color information, and/or text information are also conducted such as the comparison discussed above in regards to the border of the ROI. Values, such as flag bits or validation values, representing the outcome of these comparisons are also transmitted to the multiplexer 310. For example, a text validation value 324, a tissue validation value 326, and a color validation value 328 are provided. If a pixel corresponds to text information, tissue information, or color information, then a "1" is used for the respective values, and a "0" is used if the pixel does not correspond to the respective information.

The validation values 320, 324, 326, 328, and 320 are used by the multiplexer in conjunction with a predetermined chain of priority logic, as discussed above. Alternatively, a blending of information may occur. For example, the priority logic may allow both tissue information and border information to be allocated to the same pixel in which the border RGB value is a transparent color allowing tissue to be viewed beneath the border.

A tissue and/or color data value 332, a text data value 334, and a border data value 338 determine what actual RGB value will be used for each respective pixel. The grey-scale LUT 314 and the color LUT 316 receive the tissue and/or color data value 332 for any given pixel, and a RGB value is retrieved from the respective LUT based on the color and/or tissue data. The appropriate RGB value is then transmitted to the multiplexer 310. Similarly, the text data value 334 and the border data value 338 corresponding to a text RGB value and border RGB value, respectively, are transmitted to the multiplexer 310. A predetermined RGB value is chosen for the text data value 334 and the border data value 338. Alternatively, LUTs may be used for generating different RGB values for the text and border. After the multiplexer 310 receives the RGB values as well as the validation values, the multiplexer 310 outputs the appropriate color to the appropriate pixel for each pixel in every frame or multiple frames substantially at the same time. An image is displayed with a border of a ROI without using a software graphic overlay.

Figure 4:
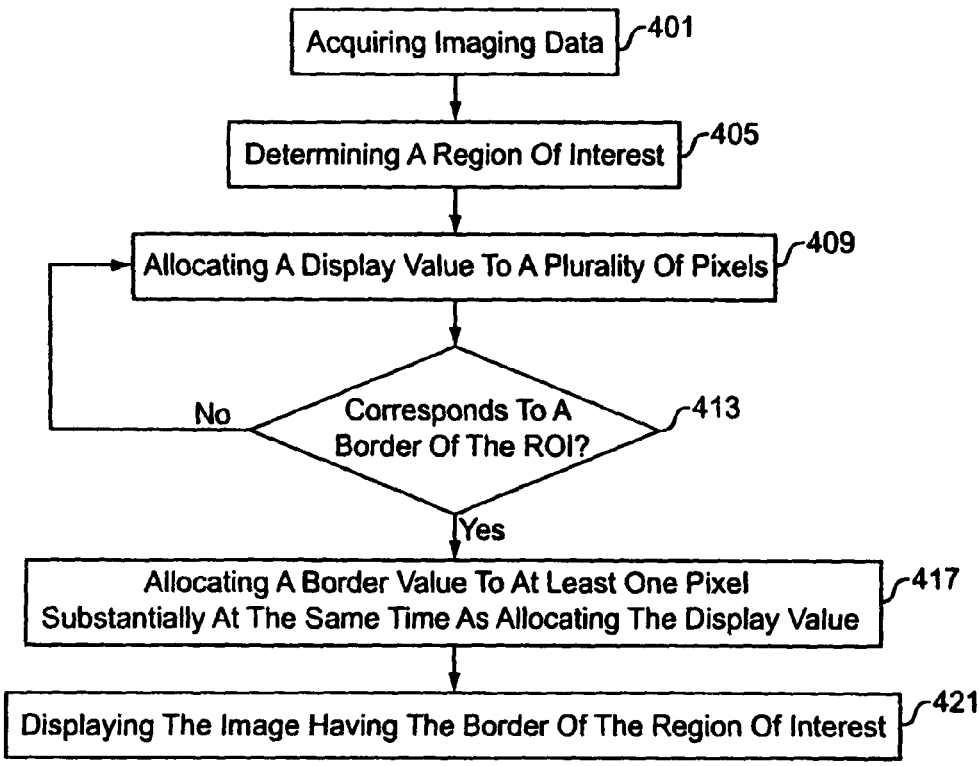
FIG. 4 is a flowchart of one embodiment of a method generating a border of a region of interest.

FIG. 4 is a flowchart of one embodiment of a method generating a border of a region of interest. In act 401, imaging data for generation of an image is acquired. For example, ultrasound imaging data, such as Doppler and/or B-mode (grey-scale) data, is acquired using a transducer, such as the transducer 102. The transducer is part of a handheld ultrasound system. For example, the handheld ultrasound system weighs less than about six pounds. Other systems may be used, such as cart or fixed systems.

In act 405, a ROI of the image is determined. For example, the ROI is determined based on a desired acquisition of color information for a section of a corresponding image. During the initial frames of the image, no ROI is determined. During imaging, a user, such as a medical professional, determines the location of a ROI by using an input device, such as the input device 126. Alternatively, the ROI is automatically determined based on image information or a default location corresponding to an area on a display, such as the display 116. Or, a predetermined ROI is entered by a user of the imaging system 100. The user may scan different parts of the image area to view color information for different areas.

In act 409, a display value is allocated to a plurality of pixels. Color or grey scale values are mapped to a plurality of pixels as a function of flow, tissue or flow and tissue information from the ultrasound data For example, values associated with color, tissue, and/or text information are allocated to the respective pixels, such as validation values 324, 326, and 328 as well as data values 332 and 334 discussed above. Each pixel location for every frame or multiple frames is compared to locations where the color, tissue, and/or text information is supposed to be displayed to determine the RGB value with which a pixel will be associated.

In act 413, a determination of whether a pixel corresponds to a border of the ROI is made. The determination is a comparison similar to the comparisons of act 409. For example, a pixel location, such as pixel location values 304 and 306, is compared to determined width, maximum, and minimum dimensions of ROI, such as the range width 211, the beam width 215, the range minimum 221, the range maximum 223, the beam minimum 225, and the beam maximum 227 discussed above. The comparisons may be implemented by any number of calculations or equations, such as the equations 1 and 2, via a comparator, such as the comparator 300, or other hardware and/or logic. Based on whether or not a pixel is in or on a border area of the border, the appropriate flag bit, such as the 320 value, is sent to a multiplexer, such as the multiplexer 310. Any function may be used to define or indicate the border.

In act 417, if the pixel is in or on a border area, a border RGB value is allocated or assigned to the at least one pixel substantially at the same time as allocating the display value based on the color or tissue information. For example, the RGB values for the text, color, and/or tissue information are sent to the multiplexer at substantially the same times as when the RGB value for the border is sent.

A chain of priority is used to select the RGB value to be displayed for each pixel. For example, text information has the most priority and border information has secondary priority. If a pixel corresponds to text, border, and tissue information, the RGB value for text will be used. However, if the pixel corresponds to border and tissue information and not text information, the RGB value for the border will be used. For example, a solid color is utilized for the border. Alternatively, video information may have equal priority. For example, tissue and border information may be given equal priority in which a RGB value representing both tissue and border information is used. This is accomplished by using a transparent color. A transparent color is used for the border, and, therefore, underlying tissue may be viewed beneath a transparent color border. Any combination of transparent colors may be used for any of the video information, such as the text, border, and/or tissue or color information. Any image data blending techniques may also be utilized.

If the pixel is not on or in the border area, the pixel is allocated a RGB value associated with the next highest priority. For example, if the pixel is outside the border of the ROI, the pixel is associated with tissue information and, therefore, the RGB value for the appropriate tissue information is used. However, if that pixel is also associated with text information, then a text RGB value will take priority. As another example, the pixel is allocated a RGB values associated with tissue and/or motion information if the pixel is not part of the border but is within the ROI.

In act 421, the image having the border of the ROI is displayed. For example, the border has a sector shape or any other geometrical shape. Any color with any density may be used for the border, such as a solid or transparent color. Alternatively, a flashing, glowing, or dynamic border may be implemented. The image is displayed in substantially real time or in a delayed time period. Because the border values are allocated substantially at the same time as when the color and/or tissue values are allocated, a border is generated without a software graphic overlay. The video images generated may not be stored in a memory of the imaging system 100 for retrieval purposes. The examination using the imaging system 100 may be recorded and displayed at a later time on the display 116 or another local or remote display. Alternatively, the examination is viewed substantially in real time with a display in a remote location via wireless or internet protocols.

The imaging system 100 includes instructions that can be executable by a processor, such as the processor 120 of FIG.

1. The instructions are stored in a computer-readable medium, such as the memory 122. The instructions implement the methods, acts, and processes described above. The instructions for implementing the processes, methods and/or techniques discussed above are provided on computer-readable storage media or memories, such as a cache, buffer, RAM, removable media, hard drive or other computer readable storage media. Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone or in combination. Likewise, processing strategies may include multiprocessing, multitasking, parallel processing and the like. In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU or system. Also, any of the features, methods, techniques described may be mixed and matched to create different systems and methodologies.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A method of providing a border for a region of interest, the method comprising:
    acquiring data from a medical scan for later generation of an image;
    determining a region of interest for the image, the region of interest having a border with a width, providing a border area;
    allocating, by a processor, display values to a plurality of pixels, respectively, based on color or tissue information from the data from the medical scan, the allocating comprising assigning red, green, and blue (RGB) or luminance and chrominance (YUV) values for the data from the scan prior to displaying the image, the plurality of pixels including pixels within and outside of the region of interest;
    where at least one pixel corresponds to the border of the region of interest to be shown on the image, allocating a border value to the at least one pixel substantially at the same time as allocating the display value based on the color or tissue information; and
    displaying the image having the border of the region of interest, the border in the image being a function of the border value without a software overlay and having the width visually separating the pixels outside of the region of interest from the pixels within the border of the region of interest, the pixels within the border and the pixels outside of the region of interest representing the color or tissue information of the data from the scan.

2. The method of claim 1, wherein displaying the image occurs in substantially real time with the acquiring.

3. The method of claim 1, wherein the data comprises ultrasound data.

4. The method of claim 1, wherein acquiring the data, determining, and allocating comprise acquiring, determining, and allocating with a handheld ultrasound system.

5. The method of claim 4, wherein the handheld ultrasound system weighs less than about six pounds.

6. The method of claim 1, wherein where the at least one pixel corresponds to a border comprises where the at least one pixel is in or on a border area of the border.

7. The method of claim 6, wherein the border area is defined by a maximum or minimum spatial extent and a width dimension.

8. The method of claim 1, wherein the region of interest comprises a sector shape.

9. The method of claim 1, wherein allocating the border value to the at least one pixel comprises designating a flag bit to the at least one pixel.

10. The method of claim 1, wherein the border value comprises a solid color or a transparent color.

11. The method of claim 1 wherein allocating comprises assigning a priority of allocating to the data from the scan and the border value for each of the pixels in the image.

12. In a non-transitory computer-readable medium having stored therein instructions executable by a processor, the instructions comprising:
    acquiring ultrasound data for later generation of an image;
    determining a region of interest to be shown on the image prior to display of the image, the region of interest having a border with a width, providing a border area;
    mapping color or grey scale values to a plurality of pixels, the mapping being a function of flow, tissue or flow and tissue information from the ultrasound data and providing the data for the image, the mapping comprising assigning the color or grey values for use by a display device from the ultrasound data prior to displaying the image, the plurality of pixels including pixels within and outside of the region of interest; and
    where at least one pixel corresponds to the border of the region of interest, allocating a border value to the at least one pixel substantially at the same time as allocating the color or grey scale value, allocating comprising incorporating the border value into the ultrasound data or the color or grey scale values for the image;
    displaying the image as a function of the color or grey scale values and the incorporated border values, the border having the width visually separating the pixels outside of the region of interest from pixels within the border of the region of interest, the pixels within the border and the pixels outside of the region of interest representing the ultrasound data.

13. The computer-readable medium of claim 12, wherein displaying the image occurs in substantially real time with the acquiring.

14. The computer-readable medium of claim 12, wherein where the at least one pixel corresponds to a border comprises where the at least one pixel is in or on a border area of the border, the border area is defined by a maximum or minimum spatial extent and a width dimension.

15. The computer-readable medium of claim 12, wherein the region of interest comprises a sector shape.

16. The computer-readable medium of claim 12, wherein allocating the border value to the at least one pixel comprises designating a flag bit to the at least one pixel.

17. The computer-readable medium of claim 12, wherein the border value comprises a solid color or a transparent color.

18. An ultrasound system for providing a border for a region of interest, the system comprising:

a transducer operable to acquire ultrasound data;

a processor configured to assign display values as a function of the ultrasound data and as a function of a border of a region of interest, the border in the display values incorporating a border color for the border, the border having a width in a border area separating a first portion from a second portion with the display values incorporating the border color, the assignment being in preparation for display of an image representing the ultrasound data, first and second portions associated with different types of ultrasound imaging; and a display configured to display an image having the border of the region of interest without a graphic overlay, the image including the border having the width that is visible and separates the first portion from the second portion, the first and second portions both representing the ultrasound data but from the different types of ultrasound imaging.

19. The system of claim 18, wherein the transducer and the processor are part of a handheld ultrasound system.

20. The system of claim 19, wherein the handheld ultrasound system weighs less than about six pounds.

21. The system of claim 19, wherein the handheld ultrasound system weighs about two pounds or less.

22. The system of claim 18, wherein the processor includes a comparator, the comparator operable to determine if at least one pixel corresponding to the display is in or on a border area of the border by comparing the at least one pixel to a maximum or minimum spatial extent and a width of the border.

23. The system of claim 18 wherein the border is defined by beam location for the scanning such that the region of interest has a shape corresponding to beams of the scan.

* * * * *